US012733665B2

(12) United States Patent
Nofar

(10) Patent No.: US 12,733,665 B2
(45) Date of Patent: Sep. 15, 2026

(54) TAHINA COMPOSITIONS AND USES THEREOF

(71) Applicant: G. NOFAR FOOD AGENCY LTD., Haifa (IL)

(72) Inventor: Gil Nofar, Haifa (IL)

(73) Assignee: G. NOFAR FOOD AGENCY LTD., Haifa (IL)

( * ) Notice: Subject to any disclaimer, the term of this patent is extended or adjusted under 35 U.S.C. 154(b) by 618 days.

(21) Appl. No.: 18/307,761

(22) Filed: Apr. 26, 2023

(65) Prior Publication Data

US 2024/0090557 A1 Mar. 21, 2024

Related U.S. Application Data

(60) Provisional application No. 63/335,755, filed on Apr. 28, 2022.

(51) Int. Cl.

| | |
|---|---|
| ***A23L 33/135*** | (2016.01) |
| ***A23L 33/105*** | (2016.01) |
| ***A61K 9/16*** | (2006.01) |
| ***A61K 35/747*** | (2015.01) |
| ***A61K 36/185*** | (2006.01) |
| ***A61K 36/53*** | (2006.01) |
| ***A61K 36/74*** | (2006.01) |
| ***A61P 25/28*** | (2006.01) |

(52) U.S. Cl.

CPC ........... *A23L 33/135* (2016.08); *A23L 33/105* (2016.08); *A61K 9/1682* (2013.01); *A61K 35/747* (2013.01); *A61K 36/185* (2013.01); *A61K 36/53* (2013.01); *A61K 36/5777* (2024.05); *A61K 36/742* (2024.05); *A61P 25/28* (2018.01)

(58) Field of Classification Search

CPC ...... A23L 33/135; A23L 35/00; A61K 9/1682
See application file for complete search history.

(56) References Cited

U.S. PATENT DOCUMENTS

| | | | |
|---|---|---|---|
| 7,767,235 | B2 | 8/2010 | Shrikhande et al. |
| 2011/0003034 | A1 | 1/2011 | Netzer |

FOREIGN PATENT DOCUMENTS

| | | | | |
|---|---|---|---|---|
| CN | 103932276 | A | | 7/2014 |
| JP | 2004000212 | A | * | 1/2004 |
| WO | WO 2014/141265 | A1 | | 9/2014 |
| WO | WO 2022/149133 | A1 | | 7/2022 |

OTHER PUBLICATIONS

Ehrnhoefer et al, EGCG redirects amyloidogenic polypeptides into unstructured, off-pathway oligomers, Nature Structural & Molecular Biology vol. 15, No. 6, pp. 558-566, 2008.

Kumar et al., Bioactive lignans from sesame (*Sesamum indicum* L.): evaluation of their antioxidant and antibacterial effects for food applications, Journal of Food Science and Technology, vol. 52, No. 5, pp. 2934-2941, 2015.

Kuriyama et al, Green tea consumption and cognitive function: a cross-sectional study from the Tsurugaya Project, The American Journal of Clinical Nutrition, vol. 83, pp. 355-361, 2006.

Rezai-Zadeh et al, Green Tea Epigallocatechin-3-Gallate (EGCG) Modulates Amyloid Precursor Protein Cleavage and Reduces Cerebral Amyloidosis in Alzheimer Transgenic Mice, The Journal of Neuroscience, vol. 25, No. 38, pp. 8807-8814, 2005.

Sivaprakasapillai et al., Effect of grape seed extract on blood pressure in subjects with the metabolic syndrome, Metabolism Clinical and Experimental, vol. 58, pp. 1743-1746, 2009.

Wang et al., Grape-Derived Polyphenolics Prevent AB Oligomerization and Attenuate Cognitive Deterioration in a Mouse Model of Alzheimer's Disease, The Journal of Neuroscience, vol. 28, No. 25, pp. 6388-6392, 2008.

Weinreb et al., Neurological mechanisms of green tea polyphenols in Alzheimer's and Parkinson's diseases, Journal of Nutritional Biochemistry, vol. 15, pp. 506-516, 2004.

Microfluidics International Corporation, 2008, in 11 pages.

Sinem et al., Production and characterisation of microfluidized olive powder. International Journal of Food Science and Technology, 59, 4907-4920. (2024).

Kiani et al., "The effect of milling process and particle size distribution on the rheological properties and structure of sesame paste." Iranian Journal of Biosystems Engineering, , 50(3), 695-703. (2019). English Abstract included.

* cited by examiner

*Primary Examiner* — Brian Gangle
*Assistant Examiner* — Lakia J Jackson-Tongue
(74) *Attorney, Agent, or Firm* — Knobbe, Martens, Olson & Bear, LLP

(57) ABSTRACT

A composition that includes tahina and probiotic bacteriais can be formulated for oral administration. The composition can also include at least one polyphenol originating in a plant other than sesame. The composition can be used in treatment of a neurodegenerative disease or disorder, such as Alzheimer's disease. A method for the preparation of the composition includes intimately mixing the tahina and the probiotic bacteria, while homogenizing without damaging the probiotic bacteria. The composition can be encapsulated within a pH-dependent enteric-coating polymer capable of protecting the mixture from gastric (stomach) acidity.

37 Claims, 2 Drawing Sheets

TAHINA COMPOSITIONS AND USES THEREOF

PRIORITY AND CROSS REFERENCE TO RELATED APPLICATIONS

The present application claims the benefit of U.S. Provisional Application No. 63/335,755, filed Apr. 28, 2022, the entire content of which being herewith incorporated by reference as if fully disclosed herein.

FIELD

The present invention relates to a composition comprising tahina, optionally at least one polyphenol originating in a plant other than sesame, and probiotic bacteria, formulated for oral administration; use thereof in treatment of a neurodegenerative disease or disorder such as Alzheimer's disease; and method for the preparation thereof.

BACKGROUND

Alzheimer's disease is a progressive neurodegenerative disorder resulting in loss of memory and dementia. Except for a few percent cases with an early onset of the disease, it is usually diagnosed at the age of 65 and more. The probability of Alzheimer's dementia rises with age from roughly 15% at age 70, to about 40% at age 90, and to 65% at age 105. As life expectancy increases, the total number people afflicted with Alzheimer's disease rapidly grows, representing an enormous financial challenge to the health care system, and still higher psychological challenge to the numerous families whose members are affected.

The cause of Alzheimer's disease is unclear. Yet, brain imaging or post-mortem examination of Alzheimer's patients shows typical brain deposits of the precipitated β-amyloid protein outside neurons (β-amyloid plaques), and an abnormal form of the protein tau accumulated inside neurons. Cholesterol transporting protein apolipoprotein E has a strong impact on risk for Alzheimer's disease, but there are many other genetic and environmental factors affecting the probability of the disease onset, including several other genes, previous injury, nutrition, and physical or social activities. Other important etiologic factors include previous inflammation episodes, as reflected by inflammatory markers.

There are no available treatments to slow Alzheimer's disease progression. Several so far approved drugs, trying to temporarily alleviate the symptoms, do not stop the fatal damage and destruction of neurons caused by the disease. The attempts to dissolve the amyloid plaques, e.g., with monoclonal antibodies, have not attained the expected results. The disease is thus handled merely by applying symptomatic treatments, or preventively recommending actively integrated lifestyle to hopefully reduce the risk for Alzheimer's disease and dementia. Since Alzheimer's disease has recently become one of the most burdensome disease or injury in the United States, even a slight improvement in the disease course or a slight slowdown in its progress will reduce the load and bring an immense relief.

Plant polyphenols are known for their health benefits, mainly as antioxidants, whether structurally classified as lignans, phenolic acids, flavonoids, or stilbenes. Said lignans include, e.g., sesamin, sesamol and sesamolin, which are present in sesame seeds. Many of said phenolic acids are known as tannins. Some tannins are hydrolysable by heating with hydrochloric acid, e.g., gallotannins and ellagitannins yielding gallic and ellagic acids, respectively; and some are non-hydrolyzable and are also referred to as condensed tannins. Pomegranates, e.g., contain ellagitannins called punicalagin and punicalin. Beside tannic acid, gallates (salts or esters of gallic acid), ellagic acid, catechin, gallocatechin, epigallocatechin, and epigallocatechin gallate (EGCG, most abundant catechin in tea), additional related materials as well as oligomers and polymers thereof have been characterized. The polyphenols are metabolized in the mammalian intestine to biologically active compounds of lower molecular weights, e.g., ellagic acid and ellagitannins providing dibenzopyranones known as urolithins. Said polyphenols may be found in plants, and are mainly extracted from their seeds, beans, whole grains, nuts, leaves, and/or flower buds.

Experimental work with green tea and EGCG indicated that orally ingested polyphenols can reach the brain and exert neuroprotective effects (Weinreb et al., 2004). In fact, in-vitro studies showed that EGCG prevented the formation of β-sheet rich aggregation products, such as amyloid fibrils, that are associated with the development of Alzheimer's disease and Parkinson disease, leading the authors to conclude that EGCG could be useful for therapy against development of these diseases (Ehrnhoefer et al., 2008).

In a different study it was shown that EGCG reduces the generation of β-amyloid peptides, suggesting that EGCG dietary supplementation may provide effective prophylaxis for Alzheimer's disease (Rezai-Zadeh et al., 2005). The potential benefit of green tea and EGCG in preventing neurodegenerative diseases has been apparently supported by a further study, showing that higher consumption of green tea is associated with lower prevalence of cognitive impairment in humans (Kuriyama et al., 2006).

Grape seed extract (GSE) is a water extract of grape seeds comprising polyphenol monomers, oligomers and polymers of catechin and of epicatechin (U.S. Pat. No. 7,767,235). EGCG and the polyphenols in GSE belong to a similar family of polyphenols, yet they are chemically distinct. Consumption of GSE was found to reduce both the systolic and diastolic blood pressures (Sivapraksapillai et al., 2009). Another study demonstrated that GSE inhibited amyloid β-protein aggregation into high-molecular-weight (HMW) oligomers in-vitro, and when orally administered in a mice model, attenuated Alzheimer's disease-type cognitive deterioration, coincidentally with reduced HMW soluble oligomeric amyloid β in the brain (Wang et al., 2008).

As have been shown, certain strains of lactic acid bacteria, e.g., *Lactobacillus plantarum* possess enzymes that, when consumed orally as probiotics (optionally protected from gastric conditions), can effectively breakdown polyphenols and tannins into smaller metabolites that are more easily absorbed from the intestine into the blood stream.

WO 2014/141265 of the present applicant discloses a composition comprising polyphenol extracts from at least two plants, e.g., grapes, tea, pomegranate, dates, and berries, and probiotic bacteria such as *Lactobacillus plantarum*, which is stated to be useful in treatment of a neurodegenerative disease such as Alzheimer's disease.

SUMMARY

In one aspect, disclosed herein is a composition comprising tahina, preferably microfluidized tahina exhibiting a particle size distribution (PSD) wherein 99% of the particles have a size of 80 μm or less, 90% of the particles have a size of 45 μm or less, and/or 50% of the particles have a size of 7 μm or less; optionally at least one polyphenol originating in a plant other than sesame, e.g., a green tea extract (GTE)

preferably comprising EGCG, GSE, or a combination thereof; and probiotic bacteria, e.g., a *Lactobacillus* species, *Bifidobacterium* species, *Enterococcus* species, *Streptococcus* species, *Pediococcus* species, *Leuconostoc* species, *Bacillus* species, *Escherichia* species, or a combination thereof, wherein said composition is formulated for oral administration.

In one particular such aspect, disclosed herein is a composition as defined above, wherein said at least one polyphenol originating in a plant other than sesame is absent; and in another particular such aspect, disclosed herein is a composition as defined above, wherein said at least one polyphenol originating in a plant other than sesame is present.

In particular embodiments, the composition disclosed herein is formulated as an oral dosage form comprising a pH-dependent enteric-coating polymer, e.g., hydroxypropyl methylcellulose (HPMC), capable of protecting said composition from gastric, i.e., stomach, acidity.

In another aspect, disclosed herein is a method for treating, attenuating the progression, preventing, or delaying the onset of clinical symptoms, of a degenerative disease or disorder, or a disease or disorder associated with mitochondria dysfunction or damage, in a subject in need thereof, said method comprising administering to said subject a therapeutically effective amount of a composition as defined above, wherein said at least one polyphenol originating in a plant other than sesame is either absent or present. In particular embodiments, the composition administered is an oral dosage form comprising a pH-dependent enteric-coating polymer capable of protecting said composition from gastric (stomach) acidity.

In particular embodiments, said degenerative disease or disorder, or disease or disorder associated with mitochondria dysfunction or damage, is a neoplastic disease, a neurodegenerative disease or disorder such as Alzheimer's disease and non-Alzheimer's dementia, a muscular dystrophy, or a disease or disorder affecting the circulatory system.

In yet another aspect, disclosed herein is a composition as defined above, i.e., a composition comprising tahina, preferably microfluidized tahina exhibiting a PSD wherein 99% of the particles have a size of 80 μm or less, 90% of the particles have a size of 45 μm or less, and/or 50% of the particles have a size of 7 μm or less; optionally at least one polyphenol originating in a plant other than sesame, e.g., a GTE preferably comprising EGCG, GSE, or a combination thereof; and probiotic bacteria, for use in treating, attenuating the progression, preventing, or delaying the onset of clinical symptoms, of a degenerative disease or disorder, or a disease or disorder associated with mitochondria dysfunction or damage. In particular embodiments, said composition is an oral dosage form comprising a pH-dependent enteric-coating polymer capable of protecting said composition from gastric (stomach) acidity.

In a further aspect, disclosed herein is a method for manufacturing of a composition as defined above, said method comprising the steps of intimately mixing said tahina, optionally said at least one polyphenol originating in a plant other than sesame, and said probiotic bacteria, while homogenizing without damaging said probiotic bacteria; and optionally encapsulating the homogeneous mixture thus obtained within a pH-dependent enteric-coating polymer capable of protecting said mixture from gastric, i.e., stomach, acidity. According to said method, the homogeneous mixture prepared may be enriched with polyphenols originating from sesame and/or gamma-aminobutyric acid (GABA), by adding one or more of sesamin, sesamol, sesamolin (sesaminol), sesame oil, and GABA, to said mixture while mixing.

In still another aspect, disclosed herein is a food product or food (nutrition) additive or supplement, comprising a composition as defined above, i.e., a composition comprising tahina, preferably microfluidized tahina exhibiting a PSD wherein 99% of the particles have a size of 80 μm or less, 90% of the particles have a size of 45 μm or less, and/or 50% of the particles have a size of 7 μm or less; optionally at least one polyphenol originating in a plant other than sesame, e.g., a GTE preferably comprising EGCG, GSE, or a combination thereof; and probiotic bacteria.

DETAILED DESCRIPTION

Figure 1A:
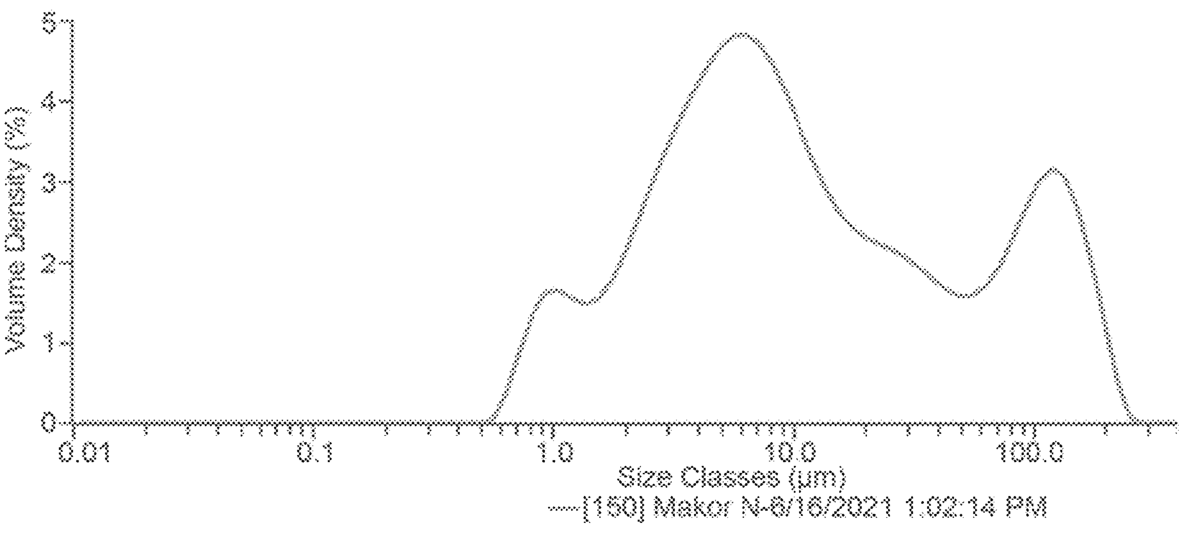
FIGS. 1A-1D show plots of volume density (%) as a function of size (μm) for the crude tahina prepared before microfluidization (FIG. 1A), and after microfluidization using the M110P Microfluidizer® (Microfluidics) according to protocol B, C or D in Example 1 (FIGS. 1B, 1C and 1D, respectively). PSD was measured using the Mastersizer 3000 laser diffraction particle size analyzer (Malvern Panalytical) with Isopar™ G as a dispersant.

It has now been found, in accordance with the present invention, that an oral composition comprising a mixture of finely dispersed tahina, polyphenols-containing plant extract such as GTE and GSE, and probiotic bacteria, when administered to a subject suffering mild dementia resulting from Alzheimer's disease, is capable of mitigating the course of the disease in said individual.

As specifically shown in the Experimental section herein, an Alzheimer's female patient characterized by rapidly progressive cognitive decline (decrease in the Mini-Mental State Examination from 20/30 to 15/30 within six months), who was suffering from depression and was usually apathetic but easily irritable, was treated during several months with a composition as referred to above. The particular composition provided comprised an overall amount of 400 mg of finely dispersed whole ground tahina, GSE, GTE and a *Lactobacillus plantarum* powder, at a weight ratio of about 30/30/16/27, respectively, filled into HPMC capsules protecting against gastric acidity, and was administered four times a day. After several weeks of treatment, the patient's mood has significantly improved compared to her state before administration commenced, and during the treatment period she was less sad, less apathetic, less irritable, and less grumpy, and the deterioration of her memory and cognitive functions has stopped. Interestingly, it seems that the patient was aware of the improvement in her mental condition as a result of said treatment, as once in a while she was keep asking for those capsules.

Surprisingly, as further found, said composition was stable in storage, wherein the probiotic *Lactobacillus* not only showed stability in the smooth tahina emulsion, but amazingly even propagated in the mixture (composition) despite the known inhibitory effects of sesame antioxidants (polyphenols) on bacterial growth (Kumar and Singh, 2015). Without being limited by any particular theory, the inventors note that the bacteria, generally known as a beneficial part of various food products and also found among gut microflora, are well preserved in the composition, and in fact metabolize some of the materials present supposedly including the polyphenols/antioxidants (those originating in the sesame seeds as well as those comprised within the GSE and GTE), which seems to be the reason for the increased bacterial count within the composition during the first week of storage. Based on this observation, it is postulated that additional polyphenol metabolites are produced by said bacteria, including metabolites having molecular weights lower than that of the original polyphenols, which are supposed to more easily spread in the subject's body and probably penetrate the blood brain barrier as well.

In one aspect, the present invention thus provides a composition comprising tahina, optionally at least one polyphenol originating in a plant other than sesame, and probiotic bacteria, wherein said composition is formulated for oral administration. In certain embodiments, said at least one polyphenol originating in a plant other than sesame is absent; and in other embodiments, said at least one polyphenol originating in a plant other than sesame is present.

The term "tahina", "tahini", "crude tahina" or "crude tahini" as used herein interchangeably refers to a Middle Eastern condiment made from either toasted or untoasted, but preferably toasted, ground sesame seeds, or from either toasted or untoasted ground sesame hulls, and containing no spices. The sesame seeds may be of any origin and of any color, i.e., white, black, brown, and red sesame seeds. Crude tahina is usually manufactured by first separating the hulls from the seeds. In some cases, the hulls may be left on the seeds, or may be removed and then added back to the hulled seeds. Grinding of the seeds, either hulled or unhulled, may be carried out using any technology known in the art, e.g., using a ball mill, millstones, macintyre grinder (as used in the chocolate industry), or a refiner conche; and it is preferably done at an outlet temperature not exceeding about 135° C., e.g., at an outlet temperature ranging from about 5 to about 130° C., from about 10 to about 120° C., from about 20 to about 110° C., or from about 30 to about 100° C. The sesame seeds may be mixed with an amount of water and optionally a salt (sodium chloride and/or potassium chloride) before toasting and/or grinding, or may be either washed with water, or soaked in water, and then dried or toasted, before grinding, inter alia so as to produce GABA. Similarly, the tahina may be mixed with an amount of water after grinding.

In certain embodiments, the tahina referred to is hulled tahina, i.e., tahina essentially consisting of ground hulled sesame seeds, i.e., sesame seeds after removal of their shells (husks). In other embodiments, said tahina is hulled tahina essentially consisting of ground hulled sesame seeds and sesame hulls, i.e., tahina made of ground hulled sesame seeds to which sesame hulls have been added while grinding. In further embodiments, said tahina is unhulled tahina also referred to herein as "whole ground tahina", i.e., tahina essentially consisting of ground unhulled sesame seeds, i.e., sesame seeds in their natural state with their shells intact, optionally in combination with hulled sesame seeds and/or sesame hulls. In yet further embodiments, said tahina essentially consists of ground sesame hulls only. Preferably, the tahina referred to is whole ground tahina. The term "essentially consisting" as used herein with respect to the tahina referred to means that said tahina substantially comprises ground sesame seeds and/or sesame hulls only, but may optionally further comprise certain amounts of water; salt (sodium chloride and/or potassium chloride) commonly added to the sesame seeds prior to the toasting process, e.g., so as to more easily separate the seeds from the hulls, if needed, and/or to improve the toasting process; and/or an emulsifier that may be added to the tahina emulsion prior to a drying process.

The tahina referred to may be in the form of a paste, i.e., liquid, or a powder, i.e., essentially dried. A dried tahina may be prepared utilizing any known technology, e.g., by mixing said paste with water and an emulsifier to obtain an emulsion, and drying said emulsion using, e.g., a spray dryer at an outlet temperature not exceeding about 120° C., preferably not exceeding about 100° C., more preferably not exceeding about 80° C., so as to prevent losses of volatile materials, as disclosed in WO/2022/149133 of the present applicant. The dried tahina obtained following such a process may still include a certain amount of water, e.g., up to 5, 6, 7, 8, 9, or 10% water, and therefore it should preferably be mixed with an anti-caking agent such as magnesium stearate and silicon dioxide.

Sesame seeds and oil are rich in polyphenols including the lignans sesamin and sesamolin (also known as sesaminol), and sesamol.

In certain embodiments, the tahina comprised within the composition disclosed herein comprises sesamin in an amount of from about 200 to about 11000 microgram/gram (mcg/g), e.g., from about 600 to about 10900 mcg/g, from about 1000 to about 10800 mcg/g, from about 1400 to about 10700 mcg/g, from about 1800 to about 10600 mcg/g, from about 2200 to about 10500 mcg/g, from about 2400 to about 10000 mcg/g, from about 2600 to about 9500 mcg/g, from about 2800 to about 9000 mcg/g, from about 3000 to about 8500 mcg/g, from about 3200 to about 8000 mcg/g, from about 3400 to about 7500 mcg/g, from about 3600 to about 7000 mcg/g, from about 3800 to about 6500 mcg/g, from about 4000 to about 6000 mcg/g, from about 4200 to about 5500 mcg/g, or from about 4400 to about 5000 mcg/g; sesamolin in an amount of from about 100 to about 8500 mcg/g, e.g., from about 200 to about 8400 mcg/g, from about 300 to about 8300 mcg/g, from about 400 to about 8200 mcg/g, from about 500 to about 8100 mcg/g, from about 600 to about 8000 mcg/g, from about 700 to about 7500 mcg/g, from about 800 to about 7000 mcg/g, from about 900 to about 6500 mcg/g, from about 1000 to about 6000 mcg/g, from about 1100 to about 5500 mcg/g, from about 1200 to about 5000 mcg/g, from about 1300 to about 4500 mcg/g, from about 1400 to about 4000 mcg/g, from about 1500 to about 3500 mcg/g, from about 1600 to about 3000 mcg/g, from about 1800 to about 2500 mcg/g, or from about 1900 to about 2000 mcg/g; and sesamol in an amount of from about 10 to about 5000 mcg/g, e.g., from about 50 to about 4500 mcg/g, from about 100 to about 4000 mcg/g, from about 150 to about 3500 mcg/g, from about 200 to about 3000 mcg/g, from about 250 to about 2500 mcg/g, from about 300 to about 2000 mcg/g, from about 400 to about 1500 mcg/g, or from about 500 to about 1000 mcg/g. In particular such embodiments, said tahina comprises sesamin in an amount of from about 3000 to about 4000 mcg/g, e.g., about 3330 mcg/g as exemplified herein; sesamolin in an amount of from about 1000 to about 2000 mcg/g, e.g., about 1320 mcg/g as exemplified herein; and sesamol.

The tahina comprised within the composition disclosed herein preferably exhibits a PSD shifted toward the lower values, meaning that a substantial part of the tahina mass is finely crushed, and the majority of the particles exhibits lower sizes. In certain embodiments, said tahina, according to any one of the embodiments above, is finely dispersed, exhibiting a PSD wherein 99% of the particles have a size of about 195 (e.g., 196 as exemplified herein) μm or less, 90% of the particles have a size of about 115 μm or less, and/or 50% of the particles have a size of about 9 (e.g., 8.9 as exemplified herein) μm or less. In preferred embodiments, said tahina is microfluidized, exhibiting a PSD wherein 99% of the particles have a size of about 80 (e.g., 77 as exemplified herein) μm or less, 90% of the particles have a size of about 45 (e.g., 44 as exemplified herein) μm or less, and/or 50% of the particles have a size of about 7 (e.g., 6.2 as exemplified herein) μm or less. The tahina, regardless of whether essentially consisting of ground hulled sesame seeds or unhulled-sesame seeds, may be microfluidized utilizing any commercially available technology such as the M-110EH-30 Microfluidizer® Processor (Microfluidics, USA) at, e.g., 22,000 pounds per square inch (PSI) using 400 μm entrance/200 μm exit (2×) followed by 200 μm entrance/100 μm exit (at least 6×).

In certain embodiments, said at least one polyphenol originating in a plant other than sesame, comprised within the composition disclosed herein, when present, is either a synthetic compound or a compound isolated and purified from a polyphenol-containing plant extract. Examples of polyphenols originating in a plant other than sesame includes, without being limited to, catechin, catechin gallate, gallocatechin gallate, epicatechin, epigallocatechin, epicatechin gallate, EGCG, quercetin, caffeine, and resveratrol.

In other embodiments, said at least one polyphenol originating in a plant other than sesame, comprised within the composition disclosed herein, when present, comprises an extract from at least one of seeds, beans, whole grains, nuts, fruits, and leaves of a polyphenol-containing plant other than sesame. Examples of such extracts include, without being limited to, those from grapes, e.g., Californian grape varieties including Ruby red grape variety, tea, pomegranates, dates, berries, olives, coffee beans, e.g., *Coffea arabica* beans and *Coffea canephora* beans, and cocoa beans.

The term "extract" as used herein refers to a polyphenol-containing extract obtained from a polyphenol-containing plant other than sesame, by extracting at least one of seeds, beans, whole grains, nuts, fruits, and leaves of said plant with a suitable (preferably edible) solvent capable of extracting polyphenols from said plant. The extraction process may be carried out following any procedure known in the art, optionally under pressure higher than the ambient pressure, and at a temperature lower than the boiling temperature of said solvent, such that the polyphenols extracted are not damaged. Examples of suitable solvents for carrying out such an extraction process include, without limiting, inorganic solvents such as fresh water, tap water, saline, and salt water; organic solvents such as methanol, ethanol, propanol, isopropanol, butanol, and t-butyl alcohol; and combinations thereof. In particular embodiments, the solvent used for extracting the polyphenols from said polyphenol-containing plant is ethanol or a combination of ethanol and water.

In particular embodiments, said at least one polyphenol originating in a plant other than sesame, comprised within the composition disclosed herein, when present, comprises a GTE, GSE, or a combination thereof. In more particular such embodiments, said at least one polyphenol comprises EGCG.

The term "probiotic bacteria" as used herein refers to live bacteria, e.g., *Lactobacillus* and *Bifidobacterium*, which when administered to a subject in adequate amounts confer a health benefit on the subject, generally by improving or restoring the gut flora.

In certain embodiments, said probiotic bacteria comprised within the composition disclosed herein is a *Lactobacillus* species such as *Lactobacillus acidophilus, Lactobacillus casei*, and *Lactobacillus plantarum*; a *Bifidobacterium* species such as *Bifidobacterium pseudocatenulatum*, e.g., *Bifidobacterium pseudocatenulatum* B7003, *Bifidobacterium animalis*, e.g., *Bifidobacterium animalis* ssp. *lactis* LAFTI (a)B94, *Bifidobacterium bifidum, Bifidobacterium longum, Bifidobacterium infantis*, and *Bifidobacterium breve; Enterococcus* species, *Streptococcus* species, *Pediococcus* species, *Leuconostoc* species, *Bacillus* species, *Escherichia* species, or a combination thereof. In a particular embodiment as exemplified herein, the probiotic bacteria comprised within the composition disclosed herein is *Lactobacillus plantarum*, e.g., *Lactobacillus plantarum* R1012-150 (Institut Rosell, Canada), formulated as lyophilized powder originally containing $1.5\times10^{11}$ bacteria.

In certain embodiments, (i) the tahina comprised within the composition disclosed herein comprises sesamin in an amount of from about 200 to about 11000 mcg/g, e.g., from about 600 to about 10900 mcg/g, from about 1000 to about 10800 mcg/g, from about 1400 to about 10700 mcg/g, from about 1800 to about 10600 mcg/g, from about 2200 to about 10500 mcg/g, from about 2400 to about 10000 mcg/g, from about 2600 to about 9500 mcg/g, from about 2800 to about 9000 mcg/g, from about 3000 to about 8500 mcg/g, from about 3200 to about 8000 mcg/g, from about 3400 to about 7500 mcg/g, from about 3600 to about 7000 mcg/g, from about 3800 to about 6500 mcg/g, from about 4000 to about 6000 mcg/g, from about 4200 to about 5500 mcg/g, or from about 4400 to about 5000 mcg/g; sesamolin in an amount of from about 100 to about 8500 mcg/g, e.g., from about 200 to about 8400 mcg/g, from about 300 to about 8300 mcg/g, from about 400 to about 8200 mcg/g, from about 500 to about 8100 mcg/g, from about 600 to about 8000 mcg/g, from about 700 to about 7500 mcg/g, from about 800 to about 7000 mcg/g, from about 900 to about 6500 mcg/g, from about 1000 to about 6000 mcg/g, from about 1100 to about 5500 mcg/g, from about 1200 to about 5000 mcg/g, from about 1300 to about 4500 mcg/g, from about 1400 to about 4000 mcg/g, from about 1500 to about 3500 mcg/g, from about 1600 to about 3000 mcg/g, from about 1800 to about 2500 mcg/g, or from about 1900 to about 2000 mcg/g; and sesamol in an amount of from about 10 to about 5000 mcg/g, e.g., from about 50 to about 4500 mcg/g, from about 100 to about 4000 mcg/g, from about 150 to about 3500 mcg/g, from about 200 to about 3000 mcg/g, from about 250 to about 2500 mcg/g, from about 300 to about 2000 mcg/g, from about 400 to about 1500 mcg/g, or from about 500 to about 1000 mcg/g; (ii) said at least one polyphenol originating in a plant other than sesame, when present, comprises an extract from at least one item selected from seeds, beans, whole grains, nuts, fruits, and leaves, of a plant other than sesame; and (iii) said probiotic bacteria is selected from a *Lactobacillus* species, *Bifidobacterium* species, *Enterococcus* species, *Streptococcus* species, *Pediococcus* species, *Leuconostoc* species, *Bacillus* species, *Escherichia* species, and a combination thereof. In particular such embodiments, the tahina comprised within said composition comprises sesamin in an amount of from about 3000 to about 4000 mcg/g, e.g., about 3330 mcg/g; and sesamolin in an amount of from about 1000 to about 2000 mcg/g, e.g., about 1320 mcg/g. Preferred such compositions are those wherein said tahina is finely dispersed and exhibiting a PSD wherein 99% of the particles have a size of 195 μm or less, 90% of the particles have a size of 115 μm or less, and/or 50% of the particles have a size of 9 μm or less.

In particular such embodiments, (i) the tahina comprised within the composition is microfluidized, exhibiting a PSD wherein 99% of the particles have a size of 80 μm or less, 90% of the particles have a size of 45 μm or less, and/or 50% of the particles have a size of 7 μm or less; (ii) said at least one polyphenol originating in a plant other than sesame, when present, comprises an extract from grapes, e.g., Californian grape varieties including Ruby red grape variety, tea, pomegranates, dates, berries, olives, coffee beans such as *Coffea arabica* beans and *Coffea canephora* beans, cocoa beans, or a combination thereof; and (iii) said *Lactobacillus* species is *Lactobacillus acidophilus, Lactobacillus casei*, or *Lactobacillus plantarum*, e.g., *Lactobacillus plantarum* R1012-150; and said *Bifidobacterium* species is *Bifidobacterium pseudocatenulatum*, e.g., *Bifidobacterium pseudocatenulatum* B7003, *Bifidobacterium animalis*, e.g., *Bifidobacterium animalis* ssp. *lactis* LAFTI(a)B94, *Bifidobacterium bifidum, Bifidobacterium longum, Bifidobacterium infantis*, or *Bifidobacterium breve*. More particular such embodiments are those wherein said at least one polyphenol comprises a GTE, GSE, or a combination thereof, preferably wherein said at least one polyphenol comprises EGCG.

According to the present invention, the composition disclosed may comprise the two or three components, i.e., said tahina, optionally said at least one polyphenol originating in a plant other than sesame, and said probiotic bacteria, at any weight ratio. In certain embodiments, the tahina comprised within the composition of the invention may constitute up to 2%, up to 10%, up to 20%, up to 30%, up to 40%, up to 50%, up to 60%, up to 70%, up to 80%, up to 90%, up to 95%, or more, by weight of said composition; said at least one polyphenol comprised within the composition of the invention, when present, may constitute up to 2%, up to 10%, up to 20%, up to 30%, up to 40%, up to 50%, up to 60%, up to 70%, up to 80%, up to 90%, up to 95%, or more, by weight of said composition; and said probiotic bacteria comprised within the composition of the invention may constitute up to 2%, up to 10%, up to 20%, up to 30%, up to 40%, up to 50%, up to 60%, up to 70%, up to 80%, up to 90%, up to 95%, or more, by weight of said composition.

In certain more specific such embodiments, said GTE is an aqueous ethanol extract obtained from *Camellia sinensis* (*C. sinensis* O. Ktze) leaves, e.g., comprising about 95% polyphenols containing at least 70% catechins and at least 40% EGCG, and about 5% caffeine; and/or said GSE is an aqueous extract obtained from Californian grape varieties including Ruby red grape variety, e.g., comprising epigallocatechin, catechin, epicatechin, EGCG, epicatechin gallate, total catechins, and quercetin, in an amount of about 0.21, 3.76, 4.94, 0.49, 0.13, 9.53, and 50.0 g/100 g, respectively. In other more specific such embodiments, the composition disclosed comprises microfluidized tahina exhibiting a PSD wherein 99% of the particles have a size of 80 μm or less, 90% of the particles have a size of 45 μm or less, and/or 50% of the particles have a size of 7 μm or less, GSE, GTE, and a *L. plantarum* powder at a weight ratio of about 30:30:16:27, respectively.

The compositions of the present invention are formulated for oral administration. Such compositions may be in the form of a liquid, e.g., a solution in an edible solvent such as ethanol, tincture, syrup, or elixir; a semi-solid; or a solid such as hard or soft capsules, tablets, caplets, pills, troches, lozenges, dispersible powder or granules, and sachets.

In certain embodiments, the compositions are in the form of matrix tablets, wherein the release of the components, i.e., at least one of said tahina, said polyphenol(s) when present, and said probiotic bacteria, is controlled by having said components diffuse through a gel formed after the swelling of a hydrophilic polymer brought into contact with dissolving liquid (in vitro) or gastro-intestinal fluid (in vivo). Many polymers have been described as capable of forming such gel, e.g., derivatives of cellulose, in particular the cellulose ethers such as hydroxypropyl cellulose, hydroxymethyl cellulose, methylcellulose or methyl hydroxypropyl cellulose, and among the different commercial grades of these ethers are those showing fairly high viscosity. In other embodiments, the tablets are formulated as bi- or multi-layer tablets, made up of two or more distinct layers of granulation compressed together with the individual layers lying one on top of another, with each separate layer containing one or more of the components, and the layers are optionally separated by an intermediate, i.e., an inactive layer such as a layer comprising one or more disintegrants.

The compositions disclosed might be formulated so as to inhibit the release of one or more of the components in the stomach, i.e., delay the release of said components(s) until at least a portion of the dosage form has traversed the stomach, in order to avoid the acidity of the gastric contents from hydrolyzing the component(s). Particular such compositions are those wherein the component(s) is coated by a pH-dependent enteric-coating polymer, also referred to herein as "acid-resistant coating", or a combination thereof. Examples of suitable pH-dependent enteric-coating polymers include, without being limited to, HPMC, hydroxypropyl methylcellulose phthalate (HPMCP), Eudragit® S (poly(methacrylicacid, methylmethacrylate), 1:2), Eudragit® L 55 (poly(methacrylicacid, ethylacrylate), 1:1), Kollicoat® (poly(methacrylicacid, ethylacrylate), 1:1), alginates, and carboxymethyl cellulose. The pH-dependent enteric-coating polymer may be present in the composition in an amount from about 5 or 10% to about 95% by weight of the entire composition.

In certain embodiments, the composition of the present invention, according to any one of the embodiments above, is thus an oral dosage form comprising a pH-dependent enteric-coating polymer, e.g., one of those listed above, capable of protecting said composition from gastric (stomach) acidity. In particular embodiments, said oral dosage is formulated as a capsule, wherein said pH-dependent enteric-coating polymer is HPMC. In a more particular such embodiment, as exemplified herein, the composition of the invention is formulated as capsules, more specifically filled within DRCAPS® capsules, which are commercially available HPMC capsules capable of protecting dietary supplement ingredients from stomach acidity.

In certain embodiments, the composition of the present invention, according to any one of the embodiments above, is formulated as a capsule, wherein said capsule is airtight so as to prevent the components from oxidizing, and thus protect the full potential of the combined healing effects of all components. The airtight feature may be attained by employing aluminum seal or aluminum laminate seal for each capsule, or alternatively by employing airtight packaging of multiple capsules, such as using sealed plastic bags.

Compositions for oral administration, regardless of their specific formulation, may further comprise one or more agents selected from sweetening agents, flavoring agents, coloring agents and preserving agents in order to provide elegant and palatable preparations. In addition, said compositions may comprise one or more acceptable excipients. For example, a tablet may comprise at least one filler such as lactose, ethylcellulose, microcrystalline cellulose, and silicified microcrystalline cellulose; at least one disintegrant such as cross-linked polyvinylpyrrolidinone; at least one binder such as polyvinylpyridone, hydroxypropylmethyl cellulose; at least one surfactant such as sodium laurylsulfate; at least one glidant such as colloidal silicon dioxide; and/or at least one anti-caking agent such as magnesium stearate and silicon dioxide.

The composition disclosed herein may be used as a medicament, i.e., a pharmaceutical or nutraceutical composition, a food (nutrition) additive or supplement, or a functional food, for, e.g., protecting against degenerative changes, more particularly neurodegenerative changes, enhancing natural immunity, and/or reducing the risk of dementia onset.

As shown herein, a composition as disclosed herein, comprising 400 mg of finely dispersed whole ground tahina, GSE, GTE and a *Lactobacillus plantarum* powder at a weight ratio of about 30/30/16/27, respectively, filled within DRCAPS® capsules, when taken four times a day, was highly effective in mitigating the clinical symptoms of Alzheimer's disease progression and/or slowing down the progression of said disease in an Alzheimer's patient characterized by rapidly progressive cognitive decline, who was suffering from depression and was usually apathetic but easily irritable.

As postulated by the inventors, the efficacy of the composition disclosed is probably attributed to a synergy between the tahina microdispersion environment, the polyphenols (both those originating in the sesame seeds and those comprised within the GSE and GTE) capable of being metabolized by bacteria, and the live probiotic bacteria. More specifically, it is assumed that said tahina is used as a growth medium in a fermentation process taking place within the composition (e.g., before storing or encapsulating within a gastric acid resistant coating), wherein said probiotic bacteria metabolize said polyphenols into small polyphenol metabolites, and upon administration of the composition and approaching the intestine, said metabolites are more easily adsorbed from the intestine into the blood stream of the subject and probably penetrate the blood brain barrier as well.

In another aspect, the present invention thus relates to a method for treating, attenuating the progression, preventing, or delaying the onset of clinical symptoms, of a degenerative disease or disorder, or a disease or disorder associated with mitochondria dysfunction or damage, in a subject in need thereof, said method comprising administering to said subject an effective (e.g., therapeutically effective) amount of a composition according to any one of the embodiments above. In certain embodiments, the method disclosed herein comprises administering said composition, wherein said at least one polyphenol originating in a plant other than sesame is absent; and in other embodiments, said method comprises administering said composition, wherein said at least one polyphenol originating in a plant other than sesame is present. Preferred embodiments are those wherein the composition administered is formulated as an oral dosage form comprising a pH-dependent enteric-coating polymer capable of protecting said composition from gastric acidity, as defined above, e.g., HPMC.

In certain embodiments, the composition administered according to the method disclosed, according to any one of the embodiments above, comprises (i) tahina comprising sesamin in an amount of from about 200 to about 11000 mcg/g, e.g., from about 600 to about 10900 mcg/g, from about 1000 to about 10800 mcg/g, from about 1400 to about 10700 mcg/g, from about 1800 to about 10600 mcg/g, from about 2200 to about 10500 mcg/g, from about 2400 to about 10000 mcg/g, from about 2600 to about 9500 mcg/g, from about 2800 to about 9000 mcg/g, from about 3000 to about 8500 mcg/g, from about 3200 to about 8000 mcg/g, from about 3400 to about 7500 mcg/g, from about 3600 to about 7000 mcg/g, from about 3800 to about 6500 mcg/g, from about 4000 to about 6000 mcg/g, from about 4200 to about 5500 mcg/g, or from about 4400 to about 5000 mcg/g; sesamolin in an amount of from about 100 to about 8500 mcg/g, e.g., from about 200 to about 8400 mcg/g, from about 300 to about 8300 mcg/g, from about 400 to about 8200 mcg/g, from about 500 to about 8100 mcg/g, from about 600 to about 8000 mcg/g, from about 700 to about 7500 mcg/g, from about 800 to about 7000 mcg/g, from about 900 to about 6500 mcg/g, from about 1000 to about 6000 mcg/g, from about 1100 to about 5500 mcg/g, from about 1200 to about 5000 mcg/g, from about 1300 to about 4500 mcg/g, from about 1400 to about 4000 mcg/g, from about 1500 to about 3500 mcg/g, from about 1600 to about 3000 mcg/g, from about 1800 to about 2500 mcg/g, or from about 1900 to about 2000 mcg/g; and sesamol in an amount of from about 10 to about 5000 mcg/g, e.g., from about 50 to about 4500 mcg/g, from about 100 to about 4000 mcg/g, from about 150 to about 3500 mcg/g, from about 200 to about 3000 mcg/g, from about 250 to about 2500 mcg/g, from about 300 to about 2000 mcg/g, from about 400 to about 1500 mcg/g, or from about 500 to about 1000 mcg/g; (ii) optionally at least one polyphenol originating in a plant other than sesame, comprising an extract from at least one item selected from seeds, beans, whole grains, nuts, fruits, and leaves, of a plant other than sesame; and (iii) probiotic bacteria selected from a *Lactobacillus* species, *Bifidobacterium* species, *Enterococcus* species, *Streptococcus* species, *Pediococcus* species, *Leuconostoc* species, *Bacillus* species, *Escherichia* species, and a combination thereof. In particular such embodiments, said tahina comprises sesamin in an amount of from about 3000 to about 4000 mcg/g, e.g., about 3330 mcg/g; and sesamolin in an amount of from about 1000 to about 2000 mcg/g, e.g., about 1320 mcg/g. Preferred such compositions are those wherein said tahina is finely dispersed and exhibiting a PSD wherein 99% of the particles have a size of 195 μm or less, 90% of the particles have a size of 115 μm or less, and/or 50% of the particles have a size of 9 μm or less.

In particular embodiments, the composition administered according to the method disclosed comprises (i) microfluidized tahina, exhibiting a PSD wherein 99% of the particles have a size of 80 μm or less, 90% of the particles have a size of 45 μm or less, and/or 50% of the particles have a size of 7 μm or less; (ii) optionally at least one polyphenol comprising an extract from grapes, e.g., Californian grape varieties including Ruby red grape variety, tea, pomegranates, dates, berries, olives, coffee beans such as *Coffea arabica* beans and *Coffea canephora* beans, cocoa beans, or a combination thereof; and (iii) probiotic bacteria selected from *Lactobacillus acidophilus, Lactobacillus casei, Lactobacillus plantarum*, e.g., *Lactobacillus plantarum* R1012-150, *Bifidobacterium pseudocatenulatum*, e.g., *Bifidobacterium pseudocatenulatum* B7003, *Bifidobacterium animalis*, e.g., *Bifidobacterium animalis* ssp. *lactis* LAFTI(a)B94, *Bifidobacterium bifidum, Bifidobacterium longum, Bifidobacterium infantis, Bifidobacterium breve*, and a combination thereof. More particular such embodiments are those wherein said at least one polyphenol comprises a GTE, GSE, or a combination thereof, preferably wherein said at least one polyphenol comprises EGCG.

The term "degenerative disease or disorder" as used herein refers to any disease or disorder in which the function or structure of the affected tissue(s) or organ(s) changes for the worse over time.

As stated above, the method of the present invention is useful, inter alia, for treating, attenuating the progression, preventing, or delaying the onset of clinical symptoms, of a disease or disorder associated with mitochondria dysfunction or damage, as mitochondria play an important role in producing and detoxifying free radicals, and the composition administered comprises a variety of antioxidants (polyphenols). The term "disease or disorder associated with mitochondrial dysfunction or damage" as used herein refers to any disease or disorder caused by a mutation or changing of structure in the mitochondrial DNA, which affects mitochondrial functioning in general and energy production in particular. Mitochondrial disorder symptoms include, e.g., poor growth, loss of muscle coordination, muscle weakness, neurological problems including seizures, autism spectrum disorder, visual and/or hearing problems, developmental delays, learning disabilities, heart, liver or kidney disease, gastrointestinal disorders such as severe constipation, diabetes, respiratory disorders, increased risk of infection, thyroid and/or adrenal dysfunction, dysfunction of the autonomic nervous system, neuropsychological changes or dementia characterized by confusion, and disorientation and memory loss. Non-limiting examples of diseases or disorders associated with mitochondrial dysfunction or damage include Kearns-Sayre syndrome (KSS), Leigh syndrome, mitochondrial DNA (mtDNA) depletion syndrome, mitochondrial encephalopathy, lactic acidosis and stroke-like episodes (MELAS) syndrome, mitochondrial neuro-gastro-intestinal encephalopathy (MNGIE), myoclonic epilepsy with ragged red fibers (MERFF), neuropathy, ataxia and retinitis pigmentosa (NARP) syndrome, Pearson syndrome, progressive external ophthalmoplegia (PEO), and autoimmune diseases common in children.

In certain embodiments, the degenerative disease or disorder, or disease or disorder associated with mitochondrial dysfunction or damage, is a neoplastic disease, e.g., a malignant neoplastic disease such as a carcinoma, sarcoma, myeloma, leukemia, and lymphoma; a neurodegenerative disease or disorder such as Alzheimer's disease, Parkinson's disease, amyotrophic lateral sclerosis, and Huntington's disease; a muscular dystrophy such as Duchenne muscular dystrophy; or a disease or disorder affecting the circulatory system.

In certain particular embodiments, the degenerative disease or disorder treated by the method of the invention is a neurodegenerative disease or disorder, more particularly Alzheimer's disease, and the composition administered is useful for, e.g., slowing down the disease or disorder progression, enhancing the subjects' physical and memory performance, and improving the subject's state of mind, i.e., mitigating the clinical symptoms of said disease or disorder. In other particular embodiments, the degenerative disease or disorder treated by the method of the invention is non-Alzheimer's dementia, and the composition administered is useful for, e.g., slowing down the disorder progression, and enhancing the subject's memory performance.

The term "subject" as used herein refers to a mammal that is either a human (herein also referred to as "individual" or "patient") or a non-human animal such as horse, dog, cat, cow, and goat.

The term "treatment" or "treating" as used herein with respect to a degenerative, e.g., neurodegenerative, disease or disorder, or a disease or disorder associated with mitochondria dysfunction or damage, refers to administration of a treatment to either a subject presenting at least one pathological phenotype (clinical symptom) manifested by said disease or disorder, or an asymptomatic subject being at risk for developing said disease or disorder (e.g., a subject being at genetic risk for Alzheimer's disease, such as one carrying apolipoprotein E (APOE)-ε4), in order to treat, reduce, attenuate, mitigate, or ameliorate said pathological phenotype, when present, and/or slow down the progression of said disease or disorder, i.e., prevent the appearance, or delay the onset, of pathological phenotypes if yet not present, or of additional pathological phenotypes, associated with said disease or disorder.

The terms "preventing" and "delaying the onset" as used herein with respect to said disease or disorder, and clinical symptoms thereof, refer to administration of the treatment to a subject, more particularly an asymptomatic subject being at risk for developing said disease or disorder (e.g., a subject being at genetic risk for Alzheimer's disease), prior to the appearance or onset of pathological phenotypes (clinical symptoms) manifested by said disease or disorder, in order to prevent the appearance or delay the onset of the clinical symptoms.

The terms "effective amount" and "therapeutically effective amount" as used herein mean an amount or dose of the composition as defined above, that is useful to treat, attenuate, or prevent a disease or disorder as referred to above. The amount must be effective to achieve the desired therapeutic effect as described above, depending, inter alia, on the type and severity of the disease or disorder to be treated and the treatment regime. The therapeutically effective amount is typically determined in appropriately designed clinical trials (dose range studies), and the person versed in the art will know how to properly conduct such trials to determine said amount. According to the present invention, the composition disclosed may be administered to said subject, e.g., once a day, twice a day, three times a day, four times a day, or more, depending, e.g., on the disease or disorder to be treated and the severity thereof. Considering that polyphenols generally react with proteins, the administration is preferably performed on an empty stomach, e.g., immediately after nocturnal sleep, or during the day but at least three hours after eating.

In yet another aspect, the present invention provides a composition according to any one of the embodiments above, regardless of whether said at least one polyphenol originating in a plant other than sesame is absent or present, for use in treating, attenuating the progression, preventing, or delaying the onset of clinical symptoms, of a degenerative disease or disorder, or a disease or disorder associated with mitochondria dysfunction or damage. Preferred embodiments are those wherein the composition used is formulated as an oral dosage form comprising a pH-dependent enteric-coating polymer capable of protecting said composition from gastric acidity, as defined above, e.g., HPMC.

In a further aspect, disclosed herein is a method for manufacturing of a composition according to any one of the embodiments above, said method comprising the steps of intimately mixing said tahina, optionally said at least one polyphenol originating in a plant other than sesame, and said probiotic bacteria, while homogenizing without damaging said probiotic bacteria; and optionally encapsulating the homogeneous mixture thus obtained within a gastric acid resistant coating, i.e., a pH-dependent enteric-coating polymer capable of protecting said mixture from gastric, i.e., stomach, acidity.

In certain embodiments, said manufacturing method further comprises the step of microdispersing said tahina optionally together with said at least one polyphenol, prior to said mixing step, to achieve a finely dispersed paste exhibiting a PSD wherein 99% of the particles have a size of 195 μm or less, 90% of the particles have a size of 115 μm or less, and/or 50% of the particles have a size of 9 μm or less. In particular embodiments, said method further comprises the step of microfluidizing said tahina, optionally together with said at least one polyphenol, prior to said mixing step, at a pressure of at least 5,000 PSI, e.g., from about 5000 PSI and up to about 40,000, 50,000, 60,000, 70,000, 80,000, 90,000, or 100,000 PSI, to obtain a dispersion exhibiting a PSD wherein 99% of the particles have a size of 80 μm or less, 90% of the particles have a size of 45 μm or less, and/or 50% of the particles have a size of 7 μm or less.

The PSD of the tahina is characterized by a percentage of particles having a size equal or less than the indicated size (diameter) in μm, or by a series of such percentages, and may be analyzed by any suitable technique, e.g., using a laser diffraction. In certain embodiments as exemplified herein, the PSD is analyzed using the Mastersizer 3000 laser diffraction particle size analyzer (Malvern Panalytical) with Isopar™ G (a high purity synthetic isoparaffinic fluid) as a dispersant. In the present case, Operational Parameters of the 42-Nasus-isopar were set as follows: Optical model default, particles RI=1.52, particles absorption index=0.1, Isopar G RI=1.42; measurement: 3 measurements of 10 seconds; pump/stirrer speed=2000 rpm; obscuration level range is 2-12 percent. Samples were prepared by rolling the container gently for 30 seconds. For the laser diffraction measurement, a Hydro EV cell was usually filled with 350 cc of the carrier. The pump speed was set to 2000 RPM and the pump was activated. A manual measurement window was opened, and requested optical model and the sample name, source and type, bulk lot reference, and operator notes were entered. Alignment of the laser was conducted, and the background was measured. Mixed sample was added into the measuring cell, filled with blank until the obscuration is in the range specified in the obscuration window. A waiting time of 20-30 seconds allowed sample dispersion. The "start" button was pressed for the first measurement. Measurements were repeated after 1 and 3 min. At the end of the measurement, the measurement window was closed, the best result was selected, and the report was printed. All reference herein to laser diffraction refer to this protocol, as well as all measurements of PSD.

In certain embodiments, said manufacturing method further comprises the step of mixing said tahina with water, so as to produce a smooth paste, and optionally with one or more emulsifiers, prior to said mixing, to obtain an emulsion. In such cases, the weight ratio between the tahina and the water mixed may be from about 1:0.1 to about 1:2.5, e.g., from about 1:0.2 to about 1:0.6, respectively. Examples of emulsifiers that may be used in this process include, without limiting, lecithin, mono- and di-glycerides, polysorbates such as Tween 80, Tween 60 and Tween 40, saponins, and rice bran extract. In a particular embodiment, the emulsifier used is rice bran extract in an amount of less than 12% of the weight of the tahina.

In certain embodiments, said manufacturing method further comprises the step of drying said tahina prior to said mixing. Such a drying process may be carried out using any suitable technology, e.g., spray drying at an outlet temperature not exceeding about 120° C., preferably not exceeding about 100° C., more preferably not exceeding about 80° C., as disclosed in WO/2022/149133.

The tahina used in the manufacturing method disclosed comprises polyphenols originating in sesame, i.e., sesamin, sesamolin and sesamol. Yet, the amount of each one of said polyphenols may vary depending on the specific sesame seeds from which said tahina has been prepared, and the type of tahina used, i.e., hulled tahina essentially consisting of ground hulled sesame seeds (to which sesame hulls have optionally been added while grinding) or unhulled tahina essentially consisting of ground unhulled sesame seeds (optionally in combination with hulled sesame seeds or sesame hulls). Thus, in certain embodiments, the homogeneous mixture prepared according to said method may be enriched with polyphenols originating from sesame and/or GABA, by adding one or more of sesamin, sesamolin, sesamol, sesame oil, and GABA, to said mixture while mixing.

Importantly for this invention, sesame seeds or tahina, and optionally the polyphenols added, are thoroughly divided into small particles before contacting with probiotic bacteria in order to increase the interface between the probiotic bacteria and the antioxidants and other components in the mixture, taking into account the known inversely proportional relation between the active particles surface and the particles size. Therefore, microdispersal or microfluidization of the sesame seeds or tahina is of special importance in this invention. The fine grinding results in a homogeneous smooth tahina paste. Another advantage of the microdispersing process is crushing of viable cells, including microorganisms which would have undesired effects in the mixture. The microdispersing process thus may advantageously obviate the need of sterilization or pasteurization of the tahina before its mixing with the probiotic bacteria. Moreover, said process lowers the viscosity of the tahina, e.g., by at least about 20%, 30%, 40%, or more, and thus results in a paste having shorter dietary fibers, that can more easily be mixed with the probiotic bacteria, and enables more efficient growth of said probiotic bacteria therein.

The viscosity of the tahina before and after the microdispersing and/or microfluidization process may be measured using any technology known in the art. In certain embodiments as exemplified herein, said viscosity is measured using a Brookfield viscometer such as the DV-II+Pro EXTRA RV, at the indicated revolutions per minute (RPM), wherein the results being expressed in Centipoise (cP).

In certain embodiments, each one of the polyphenol(s) originating in a plant other than sesame and the probiotic bacteria is independently added to the mixture as either a liquid of powder. In certain particular embodiments, both said polyphenol(s) and said probiotic bacteria are added to the mixture as powders. In other particular embodiments, both said polyphenol(s) and said probiotic bacteria are added to the mixture as liquids.

In certain embodiments, the composition prepared according to the manufacturing method disclosed herein, regardless of whether encapsulated within a gastric acid resistant coating or not, is stored under refrigerated conditions, i.e., at a temperature from about 2° C. to about 8° C., e.g., at 3, 4, 5, 6, or 7° C., or at a higher temperature, e.g., at room temperature (18-24° C.). In other embodiments, said composition is stored at a temperature below 0° C., e.g., at a temperature in between −35° C.-0° C.

In certain embodiments, the homogeneous mixture obtained following intimately mixing said tahina, optionally said at least one polyphenol originating in a plant other than sesame, and said probiotic bacteria, according to any one of the embodiments above, is left for a suitable period of time, e.g., for days, weeks, or months, under suitable humidity and gas (nitrogen/oxygen) composition and at a temperature of up to 70° C., to enable fermentation of the probiotic bacteria and formation of desired fermentation products, i.e., polyphenol metabolites, before storing or encapsulating within a gastric acid resistant coating.

In still another aspect, disclosed herein is a food product, or food (nutrition) additive or supplement (also referred to as "dietary supplement"), comprising a composition according to any one of the embodiments above, i.e., a composition comprising tahina, preferably finely dispersed tahina exhibiting a PSD wherein 99% of the particles have a size of 195 μm or less, 90% of the particles have a size of 115 μm or less, and/or 50% of the particles have a size of 9 μm or less, more preferably microfluidized tahina exhibiting a PSD wherein 99% of the particles have a size of 80 μm or less, 90% of the particles have a size of 45 μm or less, and/or 50% of the particles have a size of 7 μm or less; optionally at least one polyphenol originating in a plant other than sesame, e.g., a GTE preferably comprising EGCG, GSE, or a combination thereof; and probiotic bacteria.

In certain embodiments, the food product or dietary supplement disclosed herein comprises said composition, wherein said at least one polyphenol originating in a plant other than sesame is absent; and in other embodiments, said food product or dietary supplement comprises said composition, wherein said at least one polyphenol originating in a plant other than sesame is present.

In a similar manner to tahina, peanut butter, which is a food paste/spread made from ground dry-roasted peanuts and highly rich in polyphenols such as p-coumaric acid and isoferulic acids, may be microfluidized as shown herein with respect to tahina, e.g., using the M110P Microfluidizer® according to a protocol similar or identical to protocol D in Example 1, to provide a microfluidized product exhibiting a PSD similar to that of the microfluidized tahina. Based on these findings, and considering that all nuts are highly rich in polyphenols, it is assumed that any nut butter such as peanut butter, cashew butter, almond butter, hazelnut butter, walnut butter, chestnut butter, pecan butter, and pistachio butter in general, and a microfluidized such nut butter in particular, may be used in a composition similar to the one disclosed above, as a substitute for tahina (wherein each one of the other components independently is as defined in any one of the embodiments above).

Similarly to the tahina-containing composition, it is assumed that said nut butter will serve as a growth medium in a fermentation process taking place within the composition (e.g., before storing or encapsulating within a gastric acid resistant coating), wherein the probiotic bacteria metabolize the polyphenols (both those originating in the specific nut butter and those originating in a plant other than sesame, if present) into small polyphenol metabolites, and upon administration of the composition and approaching the intestine, said metabolites will be adsorbed from the intestine into the blood stream of the subject and probably penetrate the blood brain barrier as well.

In another aspect, thus disclosed herein is a composition comprising a nut butter (as a tahini substitute), e.g., peanut butter, cashew butter, almond butter, hazelnut butter, walnut butter, chestnut butter, pecan butter, and pistachio butter, preferably microfluidized; optionally at least one polyphenol originating in a plant other than sesame, e.g., a green tea extract (GTE) preferably comprising EGCG, GSE, or a combination thereof; and probiotic bacteria, e.g., a *Lactobacillus* species, *Bifidobacterium* species, *Enterococcus* species, *Streptococcus* species, *Pediococcus* species, *Leuconostoc* species, *Bacillus* species, *Escherichia* species, or a combination thereof, wherein said composition is formulated for oral administration. Particular such compositions are those wherein said tahini substitute is peanut butter, preferably microfluidized peanut butter. Such compositions, comprising a nut butter as a tahina substitute, are referred to herein as "tahini-substitute-containing compositions".

In one particular such aspect, disclosed herein is a tahini-substitute-containing composition as defined above, wherein said at least one polyphenol originating in a plant other than sesame is absent; and in another particular such aspect, disclosed herein is a tahini-substitute-containing composition as defined above, wherein said at least one polyphenol originating in a plant other than sesame is present.

In particular embodiments, the tahini-substitute-containing composition is formulated, e.g., as an oral dosage form comprising a pH-dependent enteric-coating polymer such as HPMC, capable of protecting said composition from gastric acidity.

In still another aspect, disclosed herein is a method for treating, attenuating the progression, preventing, or delaying the onset of clinical symptoms, of a degenerative disease or disorder, or a disease or disorder associated with mitochondria dysfunction or damage, in a subject in need thereof, said method comprising administering to said subject a therapeutically effective amount of a tahini-substitute-containing composition as defined above, wherein said at least one polyphenol originating in a plant other than sesame is either absent or present. In particular embodiments, the tahini-substitute-containing composition administered is an oral dosage form comprising a pH-dependent enteric-coating polymer capable of protecting said composition from gastric (stomach) acidity.

In yet another aspect, disclosed herein is a tahini-substitute-containing composition as defined above, i.e., a composition comprising a nut butter such as peanut butter, cashew butter, almond butter, hazelnut butter, walnut butter, chestnut butter, pecan butter, and pistachio butter, preferably microfluidized; optionally at least one polyphenol originating in a plant other than sesame, e.g., a GTE preferably comprising EGCG, GSE, or a combination thereof; and probiotic bacteria, for use in treating, attenuating the progression, preventing, or delaying the onset of clinical symptoms, of a degenerative disease or disorder, or a disease or disorder associated with mitochondria dysfunction or damage. In certain embodiments, said tahini substitute is peanut butter, preferably microfluidized peanut butter. In particular embodiments, said tahini-substitute-containing composition is an oral dosage form comprising a pH-dependent enteric-coating polymer capable of protecting said composition from gastric (stomach) acidity.

In yet a further aspect, disclosed herein is a food product or food (nutrition) additive or supplement, comprising a tahini-substitute-containing composition as defined above, i.e., a composition comprising a nut butter such as peanut butter, cashew butter, almond butter, hazelnut butter, walnut butter, chestnut butter, pecan butter, and pistachio butter, preferably microfluidized; optionally at least one polyphenol originating in a plant other than sesame, e.g., a GTE preferably comprising EGCG, GSE, or a combination thereof; and probiotic bacteria. In certain embodiments, said tahini substitute is peanut butter, preferably microfluidized peanut butter.

For purposes of clarity, and in no way limiting the scope of the teachings, unless otherwise indicated, all numbers expressing quantities, percentages or proportions, and other numerical values recited herein, should be interpreted as being preceded in all instances by the term "about", regardless of whether "about" is explicitly prepended to the numerical value. Accordingly, unless indicated to the contrary, the numerical parameters set forth in this specification are approximations that may vary by up to plus or minus 10% depending upon the desired properties to be obtained by the present invention.

The invention will now be illustrated by the following non-limiting examples.

EXAMPLES

Example 1. Efficacy of a Composition Comprising Microfluidized Tahina, GTE, GSE, and Probiotic Bacteria, in Mitigating the Clinical Symptoms of Alzheimer Disease Preparation of a Microfluidized Tahina for Use in the Composition A microfluidized tahina was prepared from crude whole ground tahina Har Bracha (Israel), following the protocols disclosed in WO/2022/149133 of the present applicant. In particular, whole grain sesame seeds (i.e., without removing the hulls) were washed with water to remove dirt, and were then transferred to a tank containing a salt solution (30 kg of salt per 1 ton of water) and soaked in said solution for a period of from about 10 minutes to about 3 hours. The seeds were then roasted, and the roasted seeds were ground into tahini using a ball mill. This process preserved the natural ratio of hulls:seeds of 7-19% on a dry matter basis usually. The whole grain tahini obtained (in the form of a paste/liquid) was processed in M110P Microfluidizer® (Microfluidics) according to the properties (tubes/channel) presented in Table 1, and was then analyzed for PSD and viscosity.

TABLE 1 exemplary microfluidization protocols

| Protocol | Previous protocol* | Channel inlet/ outlet (μm) | Number of passages | Pressure PSI |
|---|---|---|---|---|
| A | none | 400/200 | 2 | 20,000 |
| B | A | 200/100 | 3 | 20,000 |
| C | B | 200/100 | 3 | 20,000-22,000 |
| D | C | 200/100 | 3 | 20,000-22,000 |

*The protocol conducted (indicated in the left column) was preceded by the protocol indicated as "Previous protocol".

PSD was measured by a laser diffraction, using the Mastersizer 3000 laser diffraction particle size analyzer (Malvern Panalytical) with Isopar™ G as a dispersant.

Viscosity measurements were performed in Brookfield viscometer RV DV-PRO EXTRA at the indicated number of RPMs (revolutions per minute), the results being expressed as cP SC4-21 (cP); the viscometer model was DV-II+Pro EXTRA RV, the spindle was type SC4-21. The tests were conducted at room temperature. The sample container had a depth of about 60 mm and an internal diameter of about 18 mm, the internal volume being about 24 ml. After insertion of the weight, sample volume was about 7.5 ml; the liquid tahina was added in sufficient volume to cover to top of the cylinder.

Figure 1B:
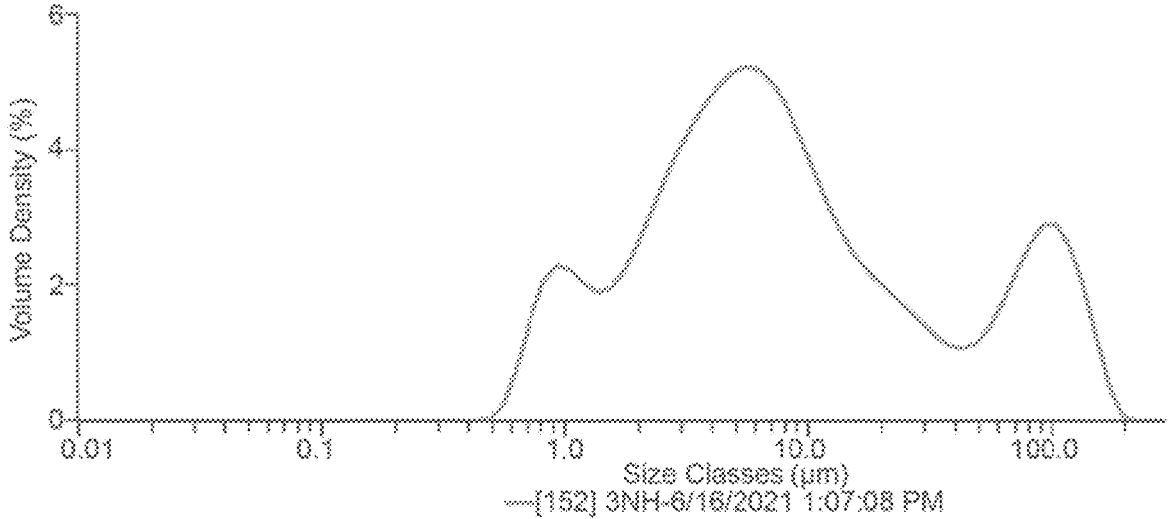
Figure 1C:
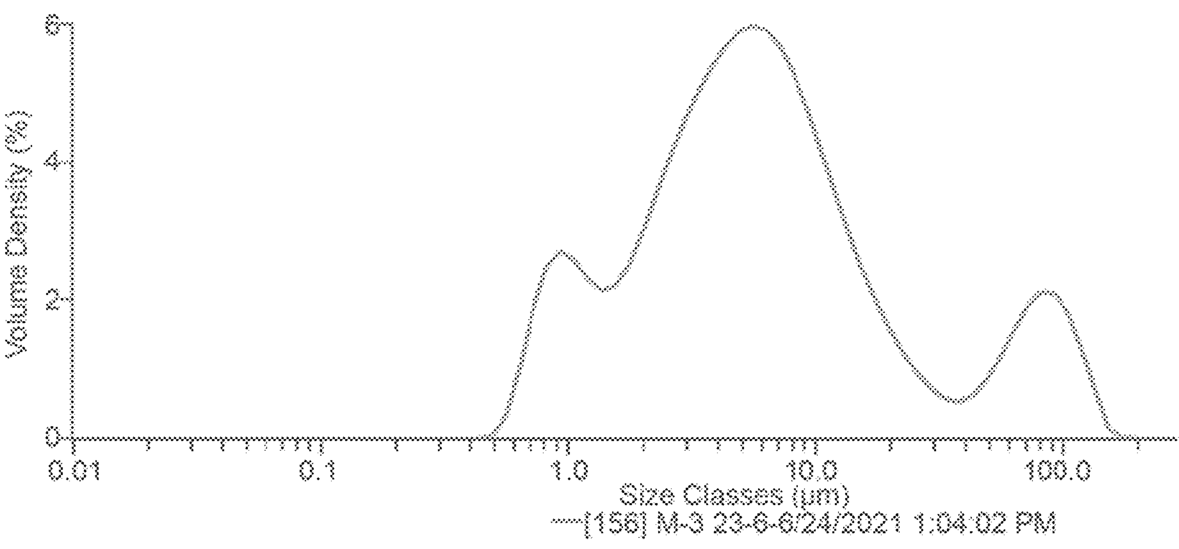
Figure 1D:
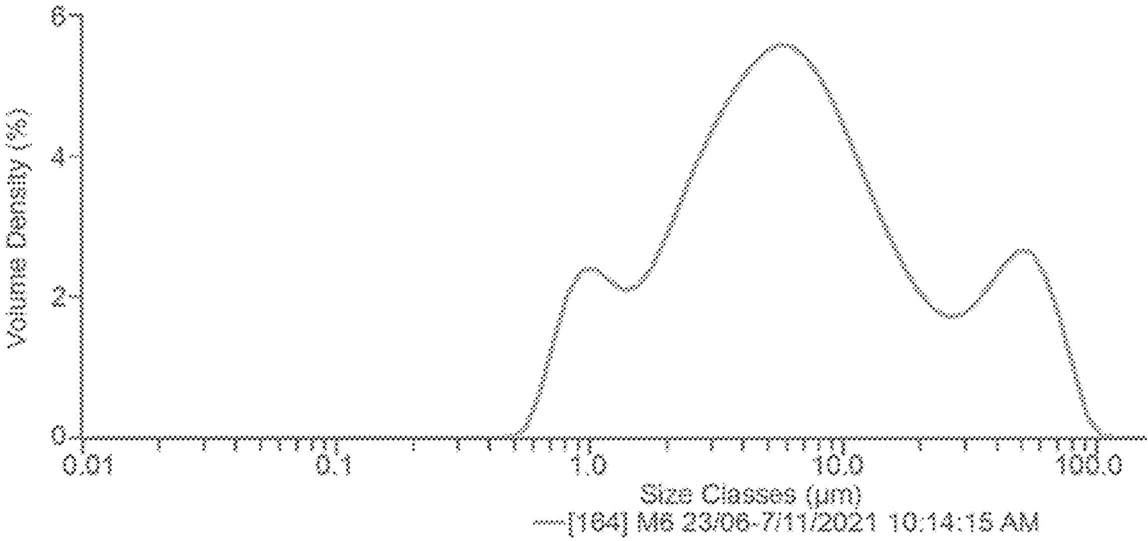

FIG. 1A shows the PSD of the tahini prepared before microfluidization, and FIGS. 1B-1D show the PSD of the tahina after microfluidization according to protocol B, C and D in Table 1, respectively (analysis and results are shown in Table 2). These data, as well as the viscosity of each one of the products prepared are shown in Table 3. As shown, the tahina sample before PSD shifting had a PSD wherein 90% of the particles had a size of 115 μm of less, and a viscosity of 4940 cP (at 5 rpm, shear 5), whereas the sample after said shifting, had a PSD wherein 90% of the particles had a size of 87 μm or less, and a viscosity of 2430 cP (at 5 rpm, shear 5).

TABLE 2

Analysis and results of the crude tahina samples tested for their PSD

| FIG. | Analysis | Results |
|---|---|---|
| 1A | Particle refractive index-—1.520 | Specific surface area-—1260 $m^2$/kg |
| | Particle absorption index-—0.100 | Span-—12.710 |
| | Dispersant refractive index-—1.420 | D [3,2]-—4.76 μm |
| | Scattering model-—Mie | D [4,3]-—33.1 μm |
| | Analysis model-—general purpose | Dv [10]-—1.84 μm |
| | Weighted residual-—1.53% | Dv [50]-—8.89 μm |
| | Laser obscuration-—12.89% | Dv [90]-—115 μm |
| | | Uniformity-—3.259 |
| | | Dv [99]-—196 μm |
| | | Dv [100]-—240 μm |
| | | Dv [95]-—147 μm |
| 1B | Particle refractive index-—1.520 | Specific surface area-—1595 $m^2$/kg |
| | Particle absorption index-—0.100 | Span-—12.791 |
| | Dispersant refractive index-—1.420 | D [3,2]-—3.76 μm |
| | Scattering model-—Mie | D [4,3]-—23.5 μm |
| | Analysis model-—general purpose | Dv [10]-—1.35 μm |
| | Weighted residual-—1.73% | Dv [50]-—6.69 μm |
| | Laser obscuration-—18.10% | Dv [90]-—86.9 μm |
| | | Uniformity-—3.039 |
| | | Dv [99]-—151 μm |
| | | Dv [100]-—186 μm |
| | | Dv [95]-—113 μm |
| 1C | Particle refractive index-—1.520 | Specific surface area-—1841 $m^2$/kg |
| | Particle absorption index-—0.100 | Span-—10.077 |
| | Dispersant refractive index-—1.420 | D [3,2]-—3.26 μm |
| | Scattering model-—Mie | D [4,3]-—15.6 μm |
| | Analysis model-—general purpose | Dv [10]-—1.19 μm |
| | Weighted residual-—1.85% | Dv [50]-—5.50 μm |
| | Laser obscuration-—16.15% | Dv [90]-—56.6 μm |
| | | Uniformity-—2.342 |
| | | Dv [99]-—121 μm |
| | | Dv [100]-—162 μm |
| | | Dv [95]-—86.4 μm |
| 1D | Particle refractive index-—1.520 | Specific surface area-—1659 $m^2$/kg |
| | Particle absorption index-—0.100 | Span-—6.690 |
| | Dispersant refractive index-—1.420 | D [3,2]-—3.62 μm |
| | Scattering model-—Mie | D [4,3]-—13.6 μm |
| | Analysis model-—general purpose | Dv [10]-—1.35 μm |
| | Weighted residual-—2.28% | Dv [50]-—6.17 μm |
| | Laser obscuration-—7.73%; | Dv [90]-—42.6 μm |
| | | Uniformity-—1.709 |
| | | Dv [99]-—76.7 μm |
| | | Dv [100]-—97.9 μm |
| | | Dv [95]-—57.1 μm |

TABLE 3

PSD of the tahini prepared before and after microfluidization according to the protocols in Table 1 (using Isopar G as a dispersant) and corresponding viscosity data

| | | | | | | | Viscosity cP SC4-21 (cP) | | | |
|---|---|---|---|---|---|---|---|---|---|---|
| | | PSD (μm) | | | | | 1 rpm | 5 rpm | 11 rpm | 22 rpm |
| FIG. | Protocol | 50% | 90% | 95% | 99% | 100% | shear1 | shear 5 | shear10 | shear20 |
| 1A | None | 8.9 | 115 | 147.2 | 196.8 | 240 | 10250 | 4940 | 4005 | unreadable |
| 1B | B | 6.7 | 87.0 | 112.7 | 151.1 | 186 | 5900 | 2430 | 1795 | 1489 |

TABLE 3-continued

PSD of the tahini prepared before and after microfluidization according to the protocols in Table 1 (using Isopar G as a dispersant) and corresponding viscosity data

| | | PSD (μm) | | | | | Viscosity cP SC4-21 (cP) | | | |
|---|---|---|---|---|---|---|---|---|---|---|
| | | | | | | | 1 rpm | 5 rpm | 11 rpm | 22 rpm |
| FIG. | Protocol | 50% | 90% | 95% | 99% | 100% | shear1 | shear 5 | shear10 | shear20 |
| 1C | C | 5.5 | 56.6 | 86.4 | 121 | 162 | 6200 | 2310 | 1632 | 1300 |
| 1D | D | 6.17 | 42.6 | 57.1 | 76.6 | 97.9 | 6100 | 2300 | 1320 | 1295 |

Preparation of the Composition

The tahina used for the preparation of the composition was the product prepared according to protocol D above.

GSE (Golden Valley Grape and Wine, UltraVin Grape Seed extract—kosher, code KGSE); GTE (Guilin Layn Natural Ingredients Corp, *Camellia Sinensis* Leaf Extract, Cas: 84650-60-2) and *Lactobacillus Plantarum* R1012-150 (Istitut Rosell and Lallemand Human Nutrition), all powders, in an amount of 30, 16 and 27 grams, respectively, were mixed together in a mixer like small food processor, and the microfluidized tahina (30 grams) was added to the mixture. The four components were mixed with pulse, while scrapping the walls of the mixer from time to time, to receive a powder with very small balls-like shape, and the mixture thus obtained was formulated as oral dosage forms, by filling in a total amount of 400 mg into HPMC capsules (DR-CAPS® capsules, net weight 0.13 g) to protect the composition against the gastric acidity.

The filled capsules were stored at 5° C. under partial vacuum (so as to prevent the content from oxidizing), and a bacterial count was performed by counting colony forming units, after 1 day, 7 days, and 45 days of storage, providing $4\times10^{10}$ (slightly lower than the manufacturer's specification, $150\times10^{9}$), $1.8\times10^{12}$ and $7.0\times10^{9}$, respectively. Although the bacterial count decreased within 45 days, it was clear that the composition supported the viable probiotics during the storage period, and within the first week it even enabled bacterial growth above the initial count. Interestingly, a certain amount of bacteria ($2.3\times10^{2}$) was detected in the stored composition even after 13 months.

The exposure of the composition, when filled in the capsules, to air was very low. As revealed by the inventors, exposure of the composition to air caused a significant decrease in the bacterial count, due to the sensitivity of the bacteria to air (bacterial count after 21 days of exposure to air was $1.0\times10^{4}$.

Treatment of an Alzheimer's Patient

The composition prepared was used for treating a subject diagnosed as suffering mild dementia resulting from Alzheimer's disease. Born in 1946, the subject had been complaining of deteriorating memory during the last 6 years. She was diagnosed as suffering from Alzheimer's disease, her Mini-Mental State Examination (MMSE) test being 20/30 in May 2021. She was usually apathetic but sometimes easily irritable. She was prescribed donapezil which she complained of. As her condition deteriorated, another assessment was performed by her geriatrician in December 2021, providing a MMSE result of 15/30. Her mood was depressed, and she stopped taking donapezil.

At that point, she started to be administered the oral dosage form prepared according to the process described above. The subject was taking four capsules a day (at least two, but preferably all four, were taken in the morning, before eating; capsules administered after breakfast, if any, were taken at least hours after eating), for a period of 5.5 months.

Results

As a result of the treatment given, the patient's mood remarkably improved within several weeks, compared to the state before the administration commenced. During the treatment period, she was less sad, less apathetic, less irritable, and less grumpy. Surprisingly, in a test conducted on May 2022, the MMSE of said patient was still 15/30, i.e., the deterioration of her memory and cognitive functions has almost stopped.

REFERENCES

Ehrnhoefer, D. E.; Bieschke, J.; Boeddrich, A.; Herbst, M.; Masino, L.; Lurz, R.; Engemann, S.; Pastore, A.; Wanker, E. E., EGCG redirects amyloidogenic polypeptides into unstructured, off-pathway oligomers. *Nature Structural & Molecular Biology,* 2008, 15(6), 558-566

Kumar. C. M.; Singh S. A., *J. Food Sci. Technol.,* 2015, 52(5), 2934-2941

Kuriyama, S.; Hozawa, A.; Ohmori, K.; Shimazu, T.; Matsui, T.; Ebihara, S.; Awata, S.; Nagatomi, T.; Arai, H.; Tsuji, I., Green tea consumption and cognitive function: a cross-sectional study from the Tsurugaya Project 1. *Am. J. Clinical Nutrition,* 2006, 83(2), 355-361

Rezai-Zadeh, K.; Shtle, D.; Sun, N.; Mori, T.; Hou, H.; Jeanniton, D.; Ehrhart, J.; Townsend, K.; Zeng, J.; Morgan, D.; Hardy, J.; Town, T.; Tan, J., Green tea epigallocatechin-3-gallate (EGCG) modulates amyloid precursor protein cleavage and reduces cerebral amyloidosis in Alzheimer transgenic mice. *J. of Neoroscience,* 2005, 25, 8807-8814

Sivapraksapillai, B.; Edirisinghe, I.; Randolph, J.; Steinberg, F.; Kappagoda, T., Effect of grape seed extract on blood pressure in subjects with the metabolic syndrome. *Metabolism Clinical and Experimental,* 2009, 58, 1743-1746

Wang, J.; Ho, L.; Zhao, W.; Ono, K.; Rosensweig, C.; Chen, L.; Humala, N.; Teplow, D. B.; Pasinetti, G. M., Grape-derived polyphenolics prevent Aβ oligomerization and attenuate cognitive deterioration in a mouse model of Alzheimer's disease. The Journal of Neuroscience, 2008, 28(25), 6388-6392

Weinreb, O.; Mandel, S.; Amit, T.; Youdim, M. B. H., Neurological mechanisms of green tea polyphenols in Alzheimer's and Parkinson's diseases. *J. Nutritional Biochemistry,* 2004, 15(9), 506-516

What is claimed is:

1. A composition comprising tahina and probiotic bacteria, formulated for oral administration, wherein said tahina has been microfluidized by passing through a fixed-geometry homogenization channel at a pressure of at least 5000 PSI.

2. The composition of claim 1, further comprising at least one polyphenol originating in a plant other than sesame.

3. The composition of claim 2, wherein said at least one polyphenol originating in a plant other than sesame comprises an extract from at least one item selected from the group consisting of seeds, beans, whole grains, nuts, fruits, and leaves, of a plant other than sesame.

4. The composition of claim 3, wherein said polyphenol comprises an extract from grapes, tea, pomegranates, dates, berries, olives, coffee beans, and/or cocoa beans.

5. The composition of claim 4, wherein said polyphenol comprises a green tea extract (GTE), grape seed extract (GSE), or a combination thereof.

6. The composition of claim 5, wherein said polyphenol comprises epigallocatechin gallate (EGCG).

7. The composition of claim 2, wherein said tahina comprises sesamin in an amount of from about 200 to about 11000 mcg/g; sesamolin in an amount of from about 100 to about 8500 mcg/g; and sesamol in an amount of from about 10 to about 5000 mcg/g, and exhibits a PSD wherein 99% of the particles have a size of 151 μm or less, 90% of the particles have a size of 87 μm or less, and/or 50% of the particles have a size of 7 μm or less, as measured by laser diffraction analysis in a wet dispersion using an non-aqueous, isoparaffinic hydrocarbon fluid as a dispersant; said at least one polyphenol originating in a plant other than sesame comprises an extract from at least one item selected from the group consisting of seeds, beans, whole grains, nuts, fruits, and leaves, of a plant other than sesame; and said probiotic bacteria are selected from the group consisting of a *Lactobacillus* species, *Bifidobacterium* species, *Enterococcus* species, *Streptococcus* species, *Pediococcus* species, *Leuconostoc* species, *Bacillus* species, *Escherichia* species, and a combination thereof.

8. The composition of claim 7, wherein said tahina exhibits a PSD wherein 99% of the particles have a size of 80 μm or less, 90% of the particles have a size of 45 μm or less, and/or 50% of the particles have a size of 7 μm or less; said polyphenol comprises an extract from grapes, tea, pomegranates, dates, berries, olives, coffee beans, and/or cocoa beans; said *Lactobacillus* species is *Lactobacillus acidophilus, Lactobacillus casei*, or *Lactobacillus plantarum*; and said *Bifidobacterium* species is selected from the group consisting of *Bifidobacterium pseudocatenulatum, Bifidobacterium animalis, Bifidobacterium bifidum, Bifidobacterium longum, Bifidobacterium infantis*, and *Bifidobacterium breve.*

9. The composition of claim 8, wherein said extract comprises a GTE, GSE, or a combination thereof.

10. The composition of claim 9, wherein said extract comprises EGCG.

11. The composition of claim 9, wherein said GTE is an aqueous ethanol extract obtained from *Camellia sinensis* leaves; and/or said GSE is an aqueous extract obtained from Californian grape varieties including Ruby red grape variety.

12. The composition of claim 11, wherein said GTE comprises about 95% polyphenols containing at least 70% catechins and at least 40% EGCG, and about 5% caffeine; and/or said GSE comprises epigallocatechin, catechin, epicatechin, EGCG, epicatechin gallate, total catechins, and quercetin, in an amount of about 0.21, 3.76, 4.94, 0.49, 0.13, 9.53, and 50.0 g/100 g, respectively.

13. The composition of claim 9, comprising tahina, GSE, GTE, and *L. plantarum* powder at a weight ratio of about 30:30:16:27, respectively.

14. The composition of claim 2, wherein said tahina has been microfluidized together with said at least one polyphenol.

15. The composition of claim 1, wherein said tahina is hulled tahina essentially consisting of ground hulled sesame seeds, hulled tahina essentially consisting of ground hulled sesame seeds in combination with sesame hulls, unhulled tahina essentially consisting of ground unhulled sesame seeds, or unhulled tahina essentially consisting of ground unhulled sesame seeds in combination with ground hulled sesame seeds and/or sesame hulls.

16. The composition of claim 3, wherein said tahina comprises sesamin in an amount of from about 200 to about 11000 mcg/g; sesamolin in an amount of from about 100 to about 8500 mcg/g; and sesamol in an amount of from about 10 to about 5000 mcg/g.

17. The composition of claim 1, wherein said probiotic bacteria are selected from the group consisting of a *Lactobacillus* species, *Bifidobacterium* species, *Enterococcus* species, *Streptococcus* species, *Pediococcus* species, *Leuconostoc* species, *Bacillus* species, *Escherichia* species, and a combination thereof.

18. The composition of claim 17, wherein said *Lactobacillus* species is *Lactobacillus acidophilus, Lactobacillus casei*, or *Lactobacillus plantarum*; and said *Bifidobacterium* species is selected from the group consisting of *Bifidobacterium pseudocatenulatum, Bifidobacterium animalis, Bifidobacterium bifidum, Bifidobacterium longum, Bifidobacterium infantis*, and *Bifidobacterium breve.*

19. The composition of claim 1, wherein said tahina comprises sesamin in an amount of from about 200 to about 11000 mcg/g; sesamolin in an amount of from about 100 to about 8500 mcg/g; and sesamol in an amount of from about 10 to about 5000 mcg/g, and exhibits a PSD wherein 99% of the particles have a size of 151 μm or less, 90% of the particles have a size of 87 μm or less, and/or 50% of the particles have a size of 7 μm or less, as measured by laser diffraction analysis in a wet dispersion using an non-aqueous, isoparaffinic hydrocarbon fluid as a dispersant; and said probiotic bacteria are selected from the group consisting of a *Lactobacillus* species, *Bifidobacterium* species, *Enterococcus* species, *Streptococcus* species, *Pediococcus* species, *Leuconostoc* species, *Bacillus* species, *Escherichia* species, and a combination thereof.

20. The composition of claim 19, wherein said tahina exhibits a PSD wherein 99% of the particles have a size of 80 μm or less, 90% of the particles have a size of 45 μm or less, and/or 50% of the particles have a size of 7 μm or less; said *Lactobacillus* species is *Lactobacillus acidophilus, Lactobacillus casei*, or *Lactobacillus plantarum*; and said *Bifidobacterium* species is selected from the group consisting of *Bifidobacterium pseudocatenulatum, Bifidobacterium animalis, Bifidobacterium bifidum, Bifidobacterium longum, Bifidobacterium infantis*, and *Bifidobacterium breve.*

21. The composition of claim 1, in the form of a liquid, semi-solid, or solid; or being an oral dosage form comprising a pH-dependent enteric-coating polymer capable of protecting said composition from gastric (stomach) acidity.

22. The composition of claim 21, wherein said pH-dependent enteric-coating polymer is selected from the group consisting of hydroxypropyl methylcellulose (HPMC), hydroxypropyl methylcellulose phthalate (HPMCP), poly(methacrylicacid, methylmethacrylate, 1:2, poly(methacrylicacid, ethylactylate, 1:1, poly(methacrylicacid, ethylacrylate, 1:1, alginates, carboxymethylcellulose, and combinations thereof.

23. The composition of claim 22, wherein said pH-dependent enteric-coating polymer is HPMC.

24. A method for the manufacturing of a composition according to claim 1, comprising intimately mixing said microfluidized tahina, and said probiotic bacteria, while homogenizing without damaging said probiotic bacteria.

25. The method of claim 24, wherein at least one polyphenol originating in a plant other than sesame is intimately mixed along with said tahina and said probiotic bacteria; or said tahina has been microfluidized together with at least one polyphenol originating in a plant other than sesame.

26. The method of claim 24, further comprising encapsulating the homogeneous mixture obtained within a pH-dependent enteric-coating polymer capable of protecting said mixture from gastric (stomach) acidity.

27. The method of claim 24, further comprising (i) mixing said microfluidized tahina with water, prior to said mixing of said microfluidized tahina and said probiotic bacteria, to obtain an emulsion; or (ii) drying said microfluidized tahina prior to said mixing of said microfluidized tahina and said probiotic bacteria.

28. The method of claim 27, wherein said drying is carried out in a spray dryer at an outlet temperature not exceeding about 120° C.

29. The method of claim 25, wherein said mixing is carried out while adding sesamin, sesamol, sesamolin, sesame oil, gamma-aminobutyric acid (GABA), or a combination thereof.

30. The method of claim 24, wherein said microfluidized tahina exhibits a PSD wherein 99% of the particles have a size of 151 μm or less, 90% of the particles have a size of 87 μm or less, and/or 50% of the particles have a size of 7 μm or less, as measured by laser diffraction analysis in a wet dispersion using an non-aqueous, isoparaffinic hydrocarbon fluid as a dispersant.

31. The method of claim 30, wherein said microfluidized tahina exhibits a PSD wherein 99% of the particles have a size of 80 μm or less, 90% of the particles have a size of 45 μm or less, and/or 50% of the particles have a size of 7 μm or less.

32. A food product or food (nutrition) additive or supplement, comprising a composition according to claim 1.

33. The composition of claim 1, wherein said tahina has been microfluidized by passing through a fixed-geometry homogenization channel at a pressure of at least 20,000 PSI.

34. The composition of claim 1, wherein said PSD is measured by laser diffraction using a Malvern-Mastersizer 3000 Wet dispersion with Hydro EV cell with Isopar G as a dispersant.

35. The composition of claim 1, wherein said tahina exhibits a particle size distribution (PSD) wherein 99% of the particles have a size of 195 μm or less, 90% of the particles have a size of 115 μm or less, and/or 50% of the particles have a size of 9 μm or less, as measured by laser diffraction analysis in a wet dispersion using an non-aqueous, isoparaffinic hydrocarbon fluid as a dispersant.

36. The composition of claim 35, wherein said tahina exhibits a particle size distribution (PSD) wherein 99% of the particles have a size of 151 μm or less, 90% of the particles have a size of 87 μm or less, and/or 50% of the particles have a size of 7 μm or less.

37. The composition of claim 36, wherein said tahina exhibits a PSD wherein 99% of the particles have a size of 80 μm or less, 90% of the particles have a size of 45 μm or less, and/or 50% of the particles have a size of 7 μm or less.

* * * * *